United States Patent [19]
Ridgeway, Jr.

[11] Patent Number: 5,878,813
[45] Date of Patent: Mar. 9, 1999

[54] APPARATUS AND METHOD FOR CAPTURING AND RETRIEVING LIQUID SAMPLE USING A WEIGHED SAMPLING DEVICE

[76] Inventor: Billy Ridgeway, Jr., 6834 Flintlock, Houston, Tex. 77040

[21] Appl. No.: 806,540

[22] Filed: Feb. 24, 1997

[51] Int. Cl.⁶ ................................................. E21B 49/08
[52] U.S. Cl. ..................... 166/162; 73/864.63; 166/264
[58] Field of Search .................................. 166/162, 264, 166/167, 168; 73/864.63

[56] References Cited

U.S. PATENT DOCUMENTS

| | | | |
|---|---|---|---|
| 782,636 | 2/1905 | Zander | 166/165 |
| 1,511,591 | 10/1924 | Colligan | 73/864.63 |
| 4,082,483 | 4/1978 | Sprenger | 166/162 |
| 4,254,830 | 3/1981 | Garney et al. | 166/162 |
| 4,438,654 | 3/1984 | Torstensson | 73/864.52 |
| 4,590,810 | 5/1986 | Hunkin et al. | 73/864.63 |
| 4,625,574 | 12/1986 | Robbins | 73/864.63 |
| 5,404,949 | 4/1995 | Voss | 166/264 |
| 5,507,194 | 4/1996 | Scacuzzo et al. | 73/864.63 |
| 5,537,881 | 7/1996 | White | 73/864.63 |
| 5,597,966 | 1/1997 | Timmons | 73/864.63 |

*Primary Examiner*—Hoang C. Dang
*Attorney, Agent, or Firm*—Gunn & Associates, P.C.

[57] ABSTRACT

An apparatus and method for collecting and retrieving liquid samples is disclosed. The sampling apparatus or bailer can reliably collect and retrieve liquid samples from a reservoir such as a liquid filled borehole. The sampling apparatus is mechanically simple, reliable, inexpensive to manufacture, and can optionally be discarded after one sampling operation thereby eliminating the time consuming and expensive step of cleaning the bailer prior to the next sampling operation. Furthermore, weighting is employed to assist in lowering the bailer into the reservoir of liquid to be sampled, wherein the weighting material is isolated from the interior sample chamber of the bailer in order to avoid contamination of the sample by the weighting material. The bailer can be easily emptied of sample liquid thereby minimizing operational costs associated with sampling activities.

23 Claims, 1 Drawing Sheet

U.S. Patent  Mar. 9, 1999  5,878,813
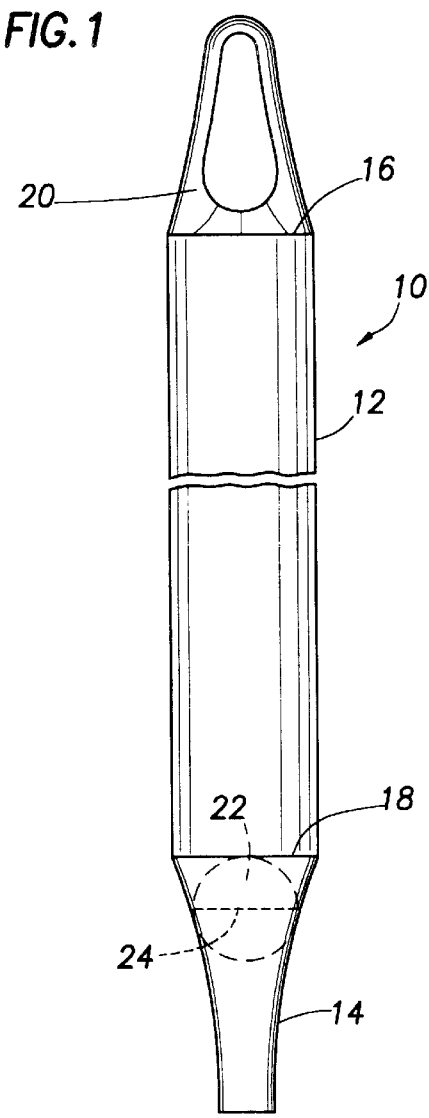
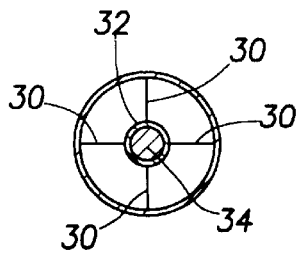
FIG. 1
FIG. 2
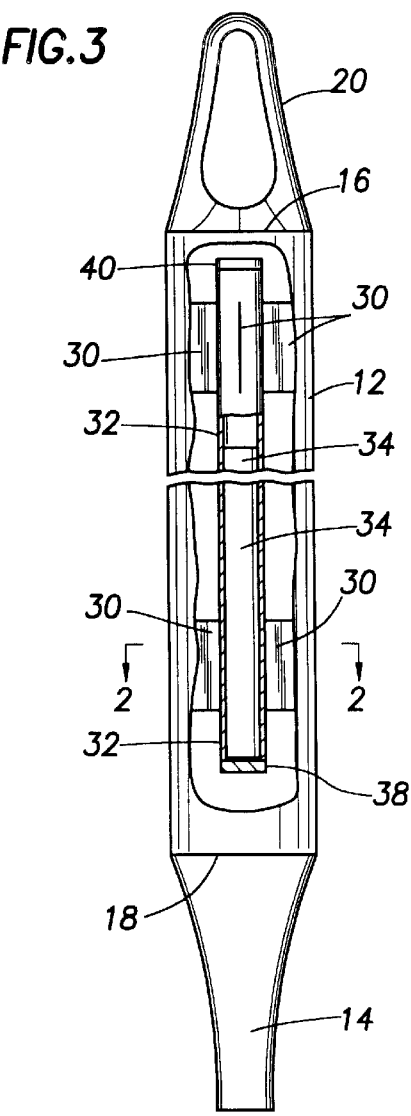
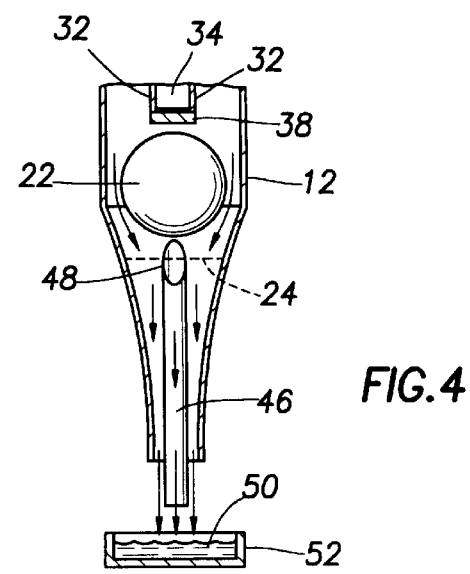
FIG. 3
FIG. 4

APPARATUS AND METHOD FOR CAPTURING AND RETRIEVING LIQUID SAMPLE USING A WEIGHED SAMPLING DEVICE

BACKGROUND OF THE INVENTION

This invention is directed toward the sampling of liquids, and more particularly directed toward the collection and retrieval of a liquid samples from a borehole or other containment structure.

BACKGROUND OF THE ART

There are a variety of devices available for collecting and retrieving samples of liquid from reservoirs. Devices which are designed to be lowered into a liquid reservoir and filled with a sample of the liquid, and to contain the sample for retrieval, are generally referred to as "bailers" in the industry. Physically, bailers are usually elongated, hollow structures which form sample chambers and which are often designed to be lowered, and subsequently retrieved, through a fill pipe of a liquid reservoir in order to reach and acquire the desired liquid sample. A typical bailer conveyance strand comprises a rope, cable or the like with one end attached to the upper end of the bailer when the bailer is in a normal operating orientation. The second end of the strand is attached to a winch or other suitable hoisting device. Bailers are often equipped with some type of check valve which allows liquid to flow into the lower end of the bailer chamber when operationally oriented. The valve also prevents the liquid from subsequently flowing out off the chamber until the sampled liquid is removed from the bailer for analysis or other processing.

U.S. Pat. No. 5,404,949 to Gene A. Voss (Voss) discloses a bailer which is designed for use in collecting and retrieving samples from a borehole and more particularly from boreholes which have been lined or "cased". In the operating orientation, the Voss device comprises an elongated, cylindrical container with a pair of orifices, isolated from the sample chamber, at the upper end which are used to affix the end or a rope or cable for conveyance. The lower end of the bailer incorporates a ball type check valve which allows liquid to flow into the chamber of the bailer, and subsequently prevents liquid from flowing out of the bailer chamber when the bailer is retrieved from the borehole. The interior of boreholes are often not "gauge" in that cracks in the casing, contaminants on the interior of the casing, and other irregularities present protrusions which can impede the conveyance of the bailer into and out of the borehole. The Voss bailer is designed to minimize the possibility of "hanging" the bailer on such borehole protrusions in that all surfaces of the bailer or rounded or otherwise contoured to assist the bailer in passing any wellbore obstacles and to minimize the possibility of bailer hanging. The Voss device does not contain additional weighting to assist in conveying the bailer into the borehole.

U.S. Pat. No. 4,438,654 to Bengt-Arne Torstensson (Torstensson) discloses a device for taking ground water samples in soil and rock. The Torstensson system comprises two main elements. The first element is permanently affixed to the lower end of a cylindrical casing which encases a borehole penetrating the rock or soil formation of interest. This device contains a channel which is terminated with a filter on the lower end and an elastomer seal at the upper end. Liquid from the rock or soil formation enters the channel through the filter. A second element is lowered into the borehole by means of a strand such as a cable or rope. The second element contains an evacuated, sealed chamber and a double ended cannula at the lower end. When the second element is lowered into the borehole such that it contacts the first element, the double ended cannula penetrates seals in the first and second elements thereby establishing a flow path between the channel of the first element and the chamber of the second element. Liquid flows from the rock or soil, thorough the filter of the first element, through the channel of the first element, through the cannula, and into the chamber of the second element. When the second element is removed from the borehole by means of the strand, the chamber of the second element is sealed thereby retaining the captured liquid sample from the rock or soil formation. The Torstensson device is relatively complex, and requires an element to be permanently affixed to the lower end of the casing or borehole liner. The Torstensson device used elastomer type seals and a cannula to fill the sample chamber, and it is known in the art that such devices are prone to leakage, especially if the seals are soluble in the sampled liquid. Furthermore, the Torstensson sample chambers must be evacuated prior to sampling thereby adding to the equipment and operational expenses of the sampling operation. Because of the relative complex sample chamber of the second element of the Torstensson system, it is usually not economically feasible to treat these chambers as "disposable" after collecting a single sample. The chamber must, therefore, be cleaned and decontaminated before the next sampling operation thereby further increasing the cost of the sampling operation.

U.S. Pat. No. 4,254,830 to Tom A. Garney and Raymond E. Roesner (Garney et al) discloses a system for evaluating geothermal wells and more specifically for collecting subsurface liquid or steam samples from geothermal drill holes. The Garney et al device utilizes an elongated probe which is conveyed within the drill hole and which contains a sample chamber. The sample chamber is initially sealed by a spring loaded inlet valve assembly. The tension of the spring can be adjusted such that the valve is opened at a predetermined pressure thereby establishing fluid communication between the interior of the drill hole and the sample chamber. Once the chamber if filled with sample, the pressure differential between chamber and drill hole is equalized such that the valve closes and the sample is contained and returned to the surface of the earth by withdrawing the sample device. The spring tension can be preset so that samples can be taken at predetermined depths within the borehole. The captured samples are often at high pressure and high temperature when returned to the surface of the earth thereby requiring special sample removal techniques to preserve the integrity of the sample.

SUMMARY OF THE INVENTION

An object of the present invention is to provide a sampling which can reliably collect and retrieve liquid samples from a reservoir such as a borehole.

A further object of the present invention is to provide a sample bailer which is inexpensive and which can optionally be discarded after one sampling operation thereby eliminating the time consuming and expensive step of cleaning the bailer prior to the next sampling operation.

A still further object of the present invention is to provide a sample bailer which is weighted to assist in lowering the bailer into the desired liquid, wherein the weighting material is isolated from the interior sample chamber in order to avoid contamination of the sample by the weighting material.

A further object of the present invention is to provide a bailer which can be easily emptied of sample liquid thereby minimizing operational costs associated with sampling activities.

An additional object of the present invention is to provide a bailer with external geometry suitable for conveyance in a borehole wherein the chance of hanging the bailer within the borehole is minimal and the chance of sampling contaminants from the wall of the borehole is also minimal.

There are other objects and advantages of the present invention that will become apparent in the following disclosure.

The bailer comprises an elongated cylinder which serves as a sample chamber in which sample liquid is collected and retained. With the bailer in operational orientation, a check valve is affixed the lower end which allows liquid to flow into the chamber, and prevents liquid from flowing out of the chamber. The check valve preferably comprises a ball or plugging device which is buoyant within the liquid to be sampled. When the bailer is submerged within the liquid, liquid flows into the chamber through an inlet spout at the bottom of the bailer, around the ball, and into the sample chamber. Once the chamber is filled, the bailer is removed from the liquid reservoir. Upon removal, the ball drops and seats against the preferably conical spout of smaller diameter thereby forming a seal which retains the collected liquid within the sample chamber. Sealing can be optionally enhanced by an o-ring at the position of contact of the ball and the spout.

The bailer sample chamber contains a preferably concentric inner cylinder which is affixed to the inner wall of the sample chamber by means of preferably two of more fins or vanes. The bottom end of the inner cylinder is sealed. The vertical extent of the inner cylinder is less than the vertical extent of the sample chamber thereby allowing free movement of the check valve ball as will be illustrated in a subsequent section. A rod or cylinder of weighting material is placed within the inner cylinder. The weighting material aids in conveying the bailer downward, by means of the force of gravity, into the reservoir of liquid to be sampled. The weighting material is especially useful in conveying the bailer downward within a borehole. The weighting material also aids in submerging the bailer within the liquid to be sampled. Once weighting rod is inserted within the inner cylinder, the top inner cylinder is sealed thereby isolating the weighting rod from the interior of the sample chamber and thereby preventing contamination of the captured sample by the rods. The weight is preferably fully enclosed or is coated to avoid rusting or corrosion. It should be understood that the weight can be adjusted by either varying the amount on metal (the preferred weight material) of a given type, or by varying the type of metal (normally iron or lead) used to form the rod. If, as an example, the weighting material is iron, it might be desirable to increase the length of the iron (the most readily available metal) weighting rod if the bailer is to be used in a very rugose borehole, or used to sample a high density liquid. Alternately, weighting can be increased by using a rod of the same length but made of a more dense weighting material (examples are well known).

The exterior shape of the bailer is void of any protrusions in order to aid in lowering and raising the bailer in a borehole. The lower end intake spout is conically tapered as discussed previously. This minimizes the chance of hanging the bailer on a borehole protrusion as the bailer is lowered into the borehole. The upper end, which contains an eyelet through which a strand such as a rope or cable is affixed for conveyance, is also tapered to minimize the chance of snaring or hanging the bailer as it is withdrawn from the borehole.

Once a sample has been "captured" within the sample chamber of the bailer, the bailer is then removed from the reservoir of sampled liquid by retrieving the deployed cable or rope using a winch, or by simply by hand. At the surface, sample can be removed from the bailer by removing the top and pouring sample from the sample chamber into a second container in which the sample is further processed and analyzed. Alternately, sample can be removed from the intake spout at the lower end by displacing the ball of the intake valve upwardly using an external protrusion. This displacement breaks the ball-spout seal and allows the captured liquid to flow from the sample chamber into the second container for analysis and processing.

The bailer is made from material which is chemically inert with respect to the sampled liquid. This, of course, prevents sample contamination by the bailer itself. Furthermore, the bailer is made using no solvents in the construction further reducing the possibility of sample contamination. All joints are preferably sonically welded. The bailer can be made of optically clear material to allow visual inspection of sampled material prior to prior to transfer of the sample from the bailer. Because of the relatively simple construction, which uses no spring valves or permanent borehole mounted elements, the cost of the bailer is relatively inexpensive thereby making it economically feasible to discard the bailer, if desired, after one use. This feature reduces the possibility of subsequent sample contamination and also reduces operating expense by eliminating the need to clean and decontaminate the bailer between uses.

BRIEF DESCRIPTION OF THE DRAWINGS

So that the manner in which the above recited features, advantages and objects of the present invention are obtained and can be understood in detail, more particular description of the invention, briefly summarized above, may be had by reference to the embodiments thereof which are illustrated in the appended drawings.

FIG. 1 shows a vertical view of the bailer in operational orientation;

FIG. 2 is a cross sectional view of the bailer showing the cylindrical sample chamber and the concentric cylindrical chamber containing a weighting rod;

FIG. 3 is a cutaway view of the bailer showing a vertical view of the concentric chamber containing a weighting rod; and FIG. 4 illustrates a method for removing a captured sample from the bailer by means of a protrusion device inserted into the intake spout.

DETAILED DESCRIPTION OF THE PREFERRED EMBODIMENTS

FIG. 1 shows the bailer identified as a whole by the numeral 10. The bailer comprises an elongated cylinder 12 which serves as a sample chamber in which sample liquid is collected and retainer. The length of the cylinder 12 is usually between 12 and 42 inches depending upon specific applications. This length can, however, be greater or less than the usual range of lengths. The bailer is illustrated in operational orientation in FIG. 1. A check valve affixed to the lower end of the chamber 12 allows liquid to flow into the chamber, and prevents liquid from flowing out of the chamber. The check valve preferably comprises a ball 22 which is buoyant within the liquid to be sampled.

When the bailer 10 is submerged within the liquid to be sampled, liquid flows into the chamber through an inlet spout 14 which is affixed to the chamber 12 at a joint 18 The joint is preferably sonically welded. More specifically, when the bailer is submerged, the ball 22 moves upward such that the maximum diameter of the ball 22 is above the broken line identified by the numeral 24. Liquid flows into the spout 14, around the ball 22, and into the sample chamber 12. Once the chamber 12 is filled, the bailer 10 is removed from the liquid reservoir that is being sampled. Upon removal, the ball 22 drops and seats against the preferably conical spout 14 of smaller diameter thereby forming a seal at the position 24. The seal between the ball 22 and the spout 14 at the position 24 retains the collected liquid within the sample chamber 12. Sealing can be optionally enhanced by an o-ring (not shown) at the point of contact 24 of the ball 22 and the spout 14. The spout 14 is preferably curving as shown in sectional view.

FIG. 2 illustrates the cross section of the bailer 10 at location A—A as denoted in FIG. 1. The outer diameter of the sample chamber 12 is typically about 1.5 inches, but can be greater or smaller depending upon the desired applications. The bailer sample chamber 12 contains a preferably concentric inner cylinder 32 which is affixed to the chamber 12 by means of preferably two or more fins or vanes or alternately with a chamber attached to the wall. Four vanes 30 spaced at 90 degrees are shown in FIG. 2. The vanes 30 are preferably sonically welded to the cylinders 32 and 12.

FIG. 3 shows a cutaway view of the interior of the bailer 10 in the region of the sample cylinder 12. The bottom end of the inner cylinder 32 is sealed with a cap 38. The vertical extent of the inner cylinder 32 is less than the vertical extent of the sample chamber 12 thereby allowing free movement of the check valve ball 22 as will be discussed in a subsequent section. A rod or cylinder 34 of weighting material is placed within the inner cylinder. A rod 34 is shown in cross section in FIG. 2. This weighting material, preferably metal, aids in conveying the bailer 10 downward, by means of the force of gravity, into the reservoir of liquid to be sampled. The weighting material is especially useful in conveying the bailer downward 10 within a borehole (not shown). The weighting material also aids in submerging the bailer 10 within the liquid to be sampled. Once weighting rod 34 is inserted within the inner cylinder the top of the inner cylinder 32 is sealed with a cap 40 thereby isolating the weighting rod 34 from the interior of the sample chamber 12 and preventing contamination of the captured sample by the weighting rod. It should be understood that the weight can be adjusted by either varying the amount of weighting material of a given type, or by varying the type of metal used to form the rod. If, as an example, the weighting material is iron, it might be desirable to increase the length of an iron weighting rod 34 if the bailer is to be used in a very rugose borehole, or used to sample a high density liquid. Alternately, weighting can be increased by using a rod 34 of the same length but made of a more dense material such as lead rather than iron.

The bailer is lowered and raised preferably by means of a strand such as a rope, cable or the like. The first end of the cable (not shown) is attached to an eyelet 20 which is attached to the chamber 12 at the joint 16. The second end of the cable is attached to a winch (not shown) such that the strand can be deployed and retrieved thereby lowering and raising the bailer 10 within the borehole. Alternately, cable can be deployed and retrieved by hand. The bailer 10 can be open at the joint 16 to remove sample liquid from the chamber 12. This, and an alternate means for removing sample, will be discussed further in a subsequent section.

The exterior shape of the bailer 10 is absent of any protrusions to aid in lowering and raising the bailer within a liquid filled borehole or other reservoir of liquid. The lower end intake spout 14 is preferably conically tapered as discussed previously. This minimizes the chance of hanging the bailer on a borehole protrusion as the bailer 10 is lowered into the borehole. The upper eyelet 20 is also tapered to minimize the chance of snaring or hanging the bailer 10 as it is withdrawn from the borehole.

Attention is now directed to both FIG. 2 and FIG. 4. Once a sample has been "captured" within the sample chamber 12, the bailer 10 is removed by retrieving the deployed cable or rope using the winch, or simply by manually retrieving the cable by hoisting. At the surface, sample can be removed from the bailer 10 by pouring from the top eyelet section 20 at the joint 16 and pouring sample from the sample chamber 12 into a second container (identified by the numeral 52 in FIG. 4) in which the sample is further processed and analyzed. Alternately, sample can be removed by way of the intake spout 14 by displacing the ball 22 of the intake valve upwardly using an external protrusion 46. This displacement breaks the ball-spout seal at the position 24 and allows the captured liquid 50 to flow from the sample chamber 12 (as indicated by arrows in FIG. 4) into the second container 52 for analysis and processing. The protrusion 46 can be hollow thereby allowing captured sample to flow through the protrusion by means of the orifice 48 as well as through the protrusion-spout annulus. The ball 22 is pinched, to coin a phrase, to move away from the seat, to enable sample flow.

The bailer 10 and, in particular, the sample chamber 12 are made from materials which are chemically inert with respect to the sampled liquid. More specifically, the chamber 12 can be constructed of 100% virgin Teflon®. Alternate materials are PVC, Viton®, Lexan® and acrylic. This, of course, prevents sample contamination by the bailer itself. Furthermore, the bailer is made using no solvents in the construction further reducing the possibility of sample contamination. Sonic welding is the preferred means for fastening elements of the bailer. The bailer can be made of optically clear material such as acrylic or Lexan® to allow visual inspection of sampled material prior to dumping of the bailer.

The construction of the disclosed bailer is relatively simple. The bailer 10 employs no spring valves, no elastomer seals, no cannula, and requires no permanent borehole mounted elements. The ball 22 is the only moving part thereby yielding a mechanically reliable bailer. Because of this relative simplicity, the cost of the bailer 10 is relatively inexpensive thereby making it economically feasible to discard the bailer, if desired, after a single sampling. This feature reduces the possibility of subsequent sample contamination and also reduces operating expense by eliminating the need to clean and decontaminate the bailer between uses.

The invention is not restricted to the embodiments described above, but can freely be varied within the scope of the appended claims.

I claim:

1. An elongate water sampling device to be lowered into a well to collect a sample comprising:
   (a) an elongate hollow cylinder having a lower end;
   (b) a lower end connected elongate and tapering hollow member having an open lower end;
   (c) a free ball in said hollow member;
   (d) wherein said ball and said hollow member define an encircling line of contact so that said ball closes said hollow member;

(e) an opening at the top of said cylinder to enable air evacuation;

(f) a top cylinder located cable connector for lowering in a well borehole, and (g) a closed and sealed chamber in said cylinder for receiving and holding a weight therein to sink said cylinder in water.

2. The apparatus of claim 1 wherein said chamber comprises a second concentric cylinder with said cylinder to define an annular water storing chamber and said cylinders are connected by a pair of radial ribs therebetween.

3. The apparatus of claim 2 wherein said second cylinder is closed at the top and bottom ends thereof to seal said weight therein.

4. The apparatus of claim 3 wherein said cylinder and second cylinder define said annular water storing chamber as an annular space above said hollow member.

5. The apparatus of claim 4 including a transverse wall across the top end of said first cylinder.

6. The apparatus of claim 5 wherein said cable connector is above said transverse wall.

7. The apparatus of claim 1 wherein said hollow member has a bottom opening of smaller size than said ball, and said ball plugs said bottom opening so that said opening permits water flow only on moving said ball to a removed location.

8. The apparatus of claim 7 wherein said ball is spherical and said hollow member has a circular cross section.

9. The apparatus of claim 8 wherein said ball and hollow member define a lower range of ball movement.

10. The apparatus of claim 9 wherein said ball is untethered to move upwardly where such movement is limited by a transverse rib across said cylinder.

11. The apparatus of claim 10 wherein said transverse rib is replicated at least two times in said cylinder so that upward ball motion is limited.

12. The apparatus of claim 11 wherein said ribs support a concentric second cylinder, and said second cylinder comprises an elongate, axially coincident closed weight receiving chamber.

13. The apparatus of claim 12 wherein said weight receiving chamber holds an elongate cylindrical metal weight.

14. The apparatus of claim 13 wherein said weight receiving chamber fully enclosed said weight therein.

15. The apparatus of claim 14 wherein said chamber is shorter in length than said cylinder.

16. The apparatus of claim 15 wherein said chamber is axially aligned by four ribs to said cylinder.

17. The apparatus of claim 16 wherein said hollow member is smaller in diameter at the lower end thereof.

18. An elongate water sampling device to be lowered into a well to collect a sample comprising:

(a) an elongate hollow cylinder having a lower end;

(b) a lower end connected elongate and tapering hollow member having an open lower end;

(c) a free ball in said hollow member, wherein (i) said ball is spherical and said hollow member has a circular cross section, (ii) said ball and hollow member define a lower range of ball movement, (iii) said ball is untethered to move upwardly where such movement is limited by a transverse rib across said cylinder, (iv) said transverse rib is replicated at least two times in said cylinder so that upward ball motion is limited, (v) said replicated ribs support a concentric second cylinder, and said second cylinder comprises an elongate, axially coincident closed weight receiving chamber, and (vi) said ball and said hollow member define an encircling line of contact so that said ball closes said hollow member;

(e) an opening at the top of said cylinder to enable air evacuation; and (f) a top cylinder located cable connector for lowering in a well borehole.

19. The apparatus of claim 18 said weight receiving chamber holds an elongate cylindrical metal weight.

20. The apparatus of claim 19 wherein said weight receiving chamber fully enclosed said weight therein.

21. The apparatus of claim 20 wherein said chamber is shorter in length than said cylinder.

22. The apparatus of claim 21 wherein said chamber is axially aligned by four ribs to said cylinder.

23. The apparatus of claim 22 wherein said hollow member is smaller in diameter at the lower end thereof.

* * * * *